(12) United States Patent
Corradi et al.

(10) Patent No.: US 8,841,503 B2
(45) Date of Patent: Sep. 23, 2014

(54) PRODUCT RECOVERY FROM ADSORPTION-SEPARATION PURGE FLUIDS

(75) Inventors: Jason T. Corradi, Arlington Heights, IL (US); James W. Harris, Palatine, IL (US); Lewis H. Pettengill, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 604 days.

(21) Appl. No.: 13/116,616

(22) Filed: May 26, 2011

(65) Prior Publication Data

US 2012/0302812 A1 Nov. 29, 2012

(51) Int. Cl.
C07C 7/12 (2006.01)
B01D 15/18 (2006.01)

(52) U.S. Cl.
CPC .............. B01D 15/1835 (2013.01); C07C 7/12 (2013.01)
USPC ............ 585/828; 585/820; 585/827; 585/826

(58) Field of Classification Search
USPC .......... 585/821, 825–828; 210/660, 662–664, 210/676, 677; 208/344–346
See application file for complete search history.

(56) References Cited

U.S. PATENT DOCUMENTS

| | | |
|---|---|---|
| 3,040,777 A | 4/1959 | Carson |
| 2,985,589 A | 5/1961 | Broughton |
| 3,422,848 A | 1/1969 | Liebman |
| 4,402,832 A | 9/1983 | Gerhold |
| 4,478,721 A | 10/1984 | Gerhold |
| 4,642,397 A | 2/1987 | Zinnen |
| 5,415,773 A | 5/1995 | Noe |
| 5,595,665 A | 1/1997 | Noe |
| 7,011,759 B1 | 3/2006 | Corradi |
| 7,208,651 B2 | 4/2007 | Frey |

*Primary Examiner* — Tam M Nguyen
(74) *Attorney, Agent, or Firm* — Mark R Willis

(57) ABSTRACT

Purge fluid from a vessel head in an adsorption process is distributed to recovery processes according to the purity of product contained in the fluid. Extract-rich fluid thus is routed directly to recovery of the extract product. Distribution preferably is determined by internal positioning of feed, desorbent and product streams in the adsorption vessel.

8 Claims, 2 Drawing Sheets

PRODUCT RECOVERY FROM ADSORPTION-SEPARATION PURGE FLUIDS

FIELD OF THE INVENTION

This invention relates generally to the processing of fluids over particulate solids. More specifically, this invention relates to the recovery of product from head-space purge fluids from a pressure vessel containing particulate solids to separate hydrocarbons.

BACKGROUND OF THE INVENTION

Petroleum refining and petrochemical processes frequently involve the processing of fluids over particulate solids contained within a pressure vessel. Internal partitions can subdivide the interior of a pressure vessel into different chambers to permit staged or multiple contacting operations within a single vessel. These partitions routinely take the form of, or are used in conjunction with, collection or distribution grids. A specific technology which illustrates the above is the simulated moving-bed ("SMB") adsorbent process described in U.S. Pat. No. 2,985,589. The process distributes and collects process streams from multiple chambers of adsorbent defined by internal partitions located within a pressure vessel and arranged as distribution/collection grids. Periodic shifting of the input and effluent streams through the chambers simulates movement of the adsorbent and permits delivery or withdrawal of the streams with a desired concentration profile. Process requirements, such as the collection and distribution of fluids, generally dictate the employment of relatively flat partitions. Such flat partitions are subject to structural damage from differential pressures of as little as 15 kPa or even less across the partition. Structural damage to a partition has the potential to create leaks across the partition or in associated distribution/collection piping.

Concomitantly, pressure vessels usually are closed by rounded "heads" at each end. The rounded head and flat interior partitions at each end of a vessel create a head space whose configuration is not suited to process purposes, risking contamination or deterioration of the process if this remains a static volume. Thus, maintaining structural integrity of interior end partitions requires pressure balancing between the head space and the adjoining volume on the process side of the partition. The head space can serve as an equalization chamber through a small opening or port in the partition communicating head fluid to and from the process chamber on the opposite side of the partition. Current technology addresses potential inefficiency in the process through head fluid passing into the process chamber and some loss in yield through process fluid passing into the head space.

The head space resulting from the flat distribution grids and a concave end is flushed by a small flow of a flush fluid, usually comprising a desorbent material, which equalizes pressure across the distribution grids. A desorbent material normally is selected so that passage of this material into the adsorbent bed through a grid opening does not contaminate the products of the process. The periodic shifting of the input and effluent streams through the chambers of adsorbent can effect a buildup of contaminants in the desorbent through leakage through the grid, however, and the addition of desorbent to the adsorbent bed through the grid opening can interfere with the optimization of purity and recovery by taking up adsorbent capacity. U.S. Pat. No. 5,595,665, incorporated herein in its entirety by reference thereto, addresses these issues by channeling the fluid generated by a head flush into a low volume chamber (referred to herein as "snorkel") in the head space and withdrawing fluid from the pressure vessel through the snorkel. Withdrawing fluid generated by the head flush and channeling the fluid through the snorkel reduces or eliminates the circulation of fluid between the equalization chamber and the adjacent process chamber and minimizes the amount of contamination that can result from any circulation of fluid resulting from pressure fluctuations and provides a non-contaminating path for withdrawing leakage from the equalization chamber of the vessel.

This known art controls contaminants in the fluid withdrawn from the snorkel. However, it does not address the resulting opportunity to recover valuable product which otherwise would be compromised in purity in the snorkel fluid.

SUMMARY OF THE INVENTION

A broad embodiment of the present invention comprises a process for the adsorption-separation of a feed stream into an extract product, containing a defined ratio of extract to impurities, from a raffinate product, in which a head-flush purge fluid is removed from a process vessel containing an adsorption bed and at least one equalization chamber, comprising passing an internal process fluid through into the equalization chamber in a process vessel having at least one rounded head, passing a head-flush fluid into the equalization chamber, and withdrawing a head-flush purge from the equalization chamber comprising varying ratios of the extract and impurities to a withdrawal pump, measuring the contained ratio of extract to impurities in the purge, and distributing the purge through a valving system to (a) the raffinate product when the weight ratio of extract to impurities in the purge is less than the weight ratio in the extract product, and (b) the extract product when the weight ratio of extract to impurities in the purge is substantially equal to or greater than the weight ratio in the extract product, and, (c) repeating steps (a) and (b) according to the determination of the weight ratio of extract to impurities in the purge.

A more specific embodiment of the process is a process for the adsorption-separation of a mixed-$C_8$-aromatics feed stream into an para-xylene product containing a defined ratio of para-xylene to $C_8$-aromatic impurities and a raffinate product, in which a head-flush purge fluid is removed from a process vessel containing an adsorption bed and at least one equalization chamber, comprising passing an internal process fluid through into the equalization chamber in a process vessel having at least one rounded head, passing a head-flush fluid into the equalization chamber, and withdrawing a head-flush purge from the equalization chamber comprising varying ratios of para-xylene and impurities, measuring the contained ratio of para-xylene to impurities in the purge, and distributing the purge through a valving system to (a) the raffinate product when the weight ratio of para-xylene to impurities in the purge is less than the weight ratio in the extract product, and, (b) the extract product when the weight ratio of para-xylene to impurities in the purge is substantially equal to or greater than the weight ratio in the extract product, and, (c) repeating steps (a) and (b) according to the determination of the weight ratio of para-xylene to impurities in the purge.

A yet more specific embodiment comprises a process for the adsorption-separation of a mixed-$C_8$-aromatics feed stream into a meta-xylene product containing a defined ratio of meta-xylene to $C_8$-aromatic impurities and a raffinate product, in which a head-flush purge fluid is removed from a process vessel containing an adsorption bed and at least one equalization chamber, comprising passing an internal process fluid through into the equalization chamber in a process vessel having at least one rounded head, passing a head-flush fluid into the equalization chamber, and withdrawing a head-flush purge from the equalization chamber comprising varying ratios of meta-xylene and impurities, measuring the contained ratio of meta-xylene to impurities in the purge, and distributing the purge through a valving system to (a) the raffinate product when the weight ratio of meta-xylene to impurities in the purge is less than the weight ratio in the extract product, and, (b) the extract product when the weight ratio of meta-xylene to impurities in the purge is substantially equal to or greater than the weight ratio in the extract product, and, (c) repeating steps (a) and (b) according to the determination of the weight ratio of meta-xylene to impurities in the purge.

Additional objects, embodiments, and details of the invention are set forth in the following detailed description of the invention.

DETAILED DESCRIPTION OF THE INVENTION

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention without so limiting it, is the recovery of para-xylene and/or meta-xylene from mixtures of $C_8$ aromatics. Such $C_8$ aromatics usually are derived within an aromatics complex by the catalytic reforming of naphtha followed by extraction and fractionation, or by transalkylation or isomerization of aromatics-rich streams in such complexes; the $C_8$ aromatics generally comprise a mixture of xylene isomers and ethylbenzene. Processing of $C_8$ aromatics simulated-moving-bed adsorption generally is directed to the recovery of high-purity para-xylene or high-purity meta-xylene; high purity usually is defined as at least 99.5 wt.-% of the desired product, and preferably at least 99.7 wt.-%.

The invention normally is employed in an adsorptive separation process which simulates countercurrent movement of the adsorbent and surrounding liquid as described above, but it may also be practiced in a cocurrent continuous process, like that disclosed in U.S. Pat. No. 4,402,832 and U.S. Pat. No. 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals. Countercurrent moving-bed or simulated-moving-bed countercurrent flow systems have a much greater separation efficiency for such separations than fixed-bed systems, as adsorption and desorption operations are continuously taking place with a continuous feed stream and continuous production of extract and raffinate. A thorough explanation of simulated-moving-bed processes is given in the Adsorptive Separation section of the Kirk-Othmer Encyclopedia of Chemical Technology at page 563.

Figure 1:
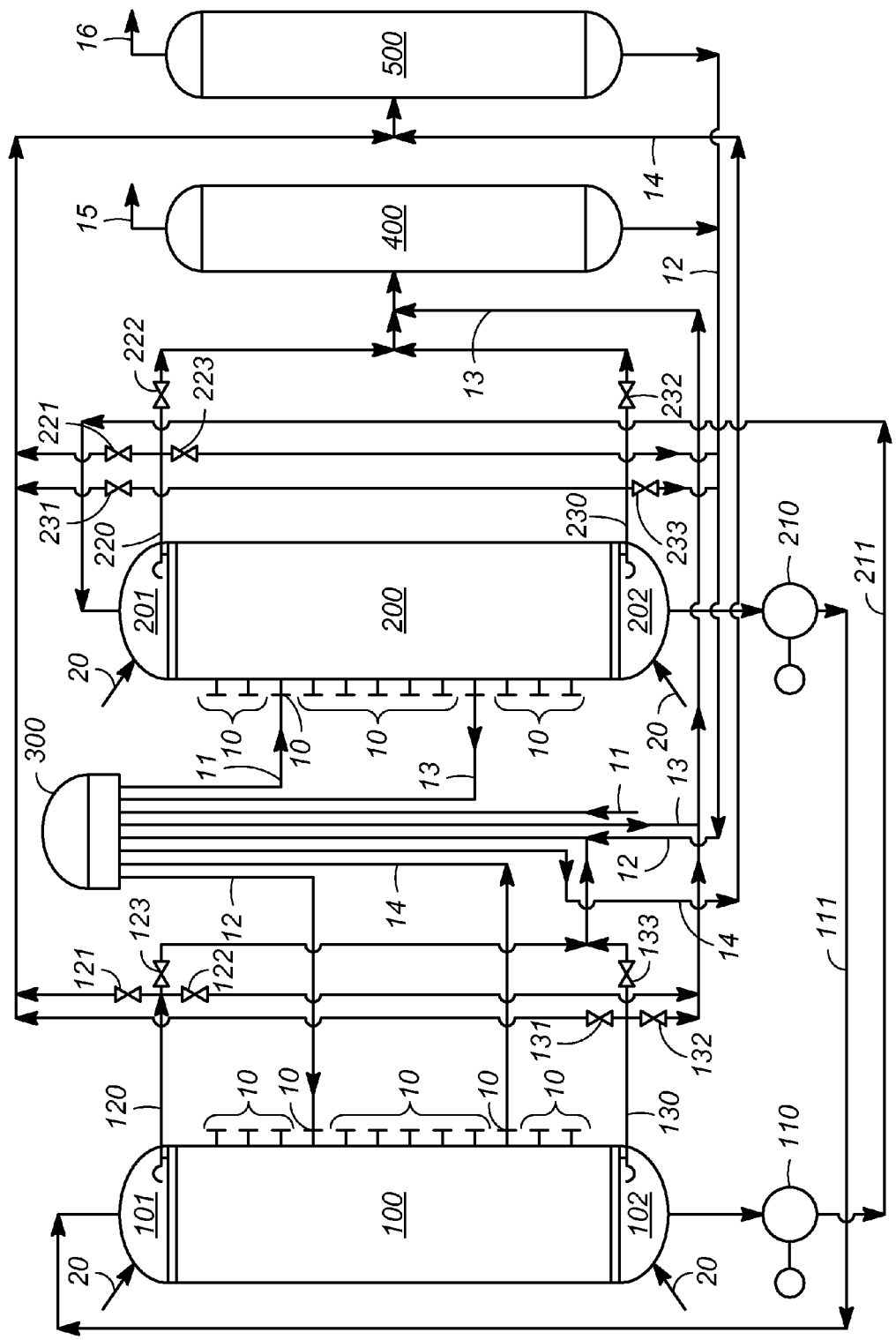
FIG. 1 is a schematic diagram of a simulated moving bed adsorption process using a heavy desorbent and comprising the features of the invention.

FIG. 1 is a schematic diagram of a simulated-moving-bed adsorption process employing the present invention. The process sequentially contacts a feed stream 11 with adsorbent contained in the vessels and a desorbent 12 to separate an extract stream 14 from a raffinate stream 13. In the simulated-moving-bed countercurrent flow system, progressive shifting of multiple liquid feed and product access points downward through an adsorbent chamber simulate the upward movement of adsorbent contained in the chamber. The adsorbent in a simulated-moving-bed adsorption process is contained in multiple beds in one or more vessels; two vessels 100 and 200 in series are shown in FIG. 1. Each vessel contains multiple beds of adsorbent contacted through a number of access points 10 relating to the number of beds of adsorbent; the position of the feed stream 11, desorbent input 12, extract stream 14 and raffinate stream 13 are shifted along the access points to simulate a moving adsorbent bed.

One method of cyclic advancement of the input and output streams through the fixed bed of adsorbent is a manifold system in which the valves in the manifold are operated in a sequential manner to effect the shifting of the input and output streams thereby allowing a flow of fluid with respect to solid adsorbent in a countercurrent manner. A preferred mode to effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. In the present scheme as shown in FIG. 1, a rotary disc type valve 300, as characterized for example in U.S. Pat. No. 3,040,777 and U.S. Pat. No. 3,422,848, incorporated herein by reference, effects the shifting of the streams along the adsorbent chamber to simulate countercurrent flow.

Coincident with this simulated upward movement of the solid adsorbent is the movement of the liquid occupying the void volume of the packed bed of molecular sieve. So that countercurrent contact is maintained, a liquid flow down the adsorbent chamber may be provided by a pump. Circulating liquid comprising desorbent, extract and raffinate circulates through the vessels through pumps 110 and 210, returning to the adsorbent chambers respectively via conduits 111 and 211. As an active liquid access point moves through a cycle, that is, from the top of the chamber to the bottom, the chamber circulation pump moves through different zones which require different flow rates. A programmed flow controller may be provided to set and regulate these flow rates. Systems to control the flow of circulating liquid are described in U.S. Pat. No. 5,595,665, but the particulars of such systems are not essential to the present invention.

The principal streams involved in simulated-moving-bed adsorption as illustrated in FIG. 1 may be characterized as follows. A "feed stream" is a mixture containing one or more extract components and one or more raffinate components to be separated by the process. The "extract product" comprises the recovered desired component, such as para-xylene or meta-xylene having a defined purity, after recovery which usually comprises fractionation. The "extract stream" comprises a component, usually the desired product which is more selectively adsorbed by the adsorbent, along with accompanying desorbent material. The "raffinate product" comprises components, after removal of the extract product, which are less selectively adsorbed. The "raffinate stream" comprises raffinate product, along with desorbent, before fractionation. "Desorbent" refers to a material capable of desorbing an extract component, which generally is inert to the components of the feed stream and easily separable from both the extract and the raffinate.

The extract product has a purity generally defined with respect to raffinate components. For example, para-xylene product impurities may comprise other $C_8$ aromatics such as ethylbenzene, meta-xylene and ortho-xylene optionally along with nonaromatics and lighter and heavier components. Meta-xylene purity accordingly would relate to the sum of the amounts of ethylbenzene, para-xylene and ortho-xylene. The product should be of at least 99 weight-% purity according to this standard, i.e., at least a ratio of 99 extract to 1 of impurities. Preferably the weight ratio is at least 995 extract to 5 of impurities, and often at least 999 to 1. When recovering para-xylene, the purity may reflect a weight ratio to other $C_8$ aromatics of 9999 to 1 or more.

The extract stream 14 and raffinate stream 13 from the illustrated scheme contain desorbent in concentrations relative to the respective product from the process of between 0% and 100%. The desorbent generally is separated from raffinate and extract components by conventional fractionation in raffinate column 400 and extract column 500 as illustrated in FIG. 1 and returned to the process in stream 12. Each of the raffinate and extract columns comprise appurtences for condensing and separating the overhead stream and supplying heat to the bottom of the column as known in the art.

FIG. 1 shows the desorbent as bottoms from the respective column, implying that the desorbent is heavier than the extract or raffinate. Different commercial units for the separation of $C_8$ aromatics employ either light or heavy desorbents, and a unit using light desorbent is discussed later. The extract product 16 and raffinate product 15 from the process are recovered from the extract stream 14 and the raffinate stream 13 in the respective columns; the extract product from the separation of $C_8$ aromatics usually comprises principally one or both of para-xylene and meta-xylene, with the raffinate being principally non-adsorbed $C_8$ aromatics and ethylbenzene.

The positions of the input and output streams define operational zones which are useful in understanding the present invention. The adsorption zone is defined as the adsorbent located between the feed inlet stream 11 and the raffinate outlet stream 13. In this zone, the feedstock contacts the molecular sieve, an extract component is retained, and a raffinate stream is withdrawn. Since the general flow through this zone is from the feed stream which passes into the zone to the raffinate stream which passes out of the zone, the flow in this zone is considered to be a downstream direction when proceeding from the feed inlet stream 11 to the raffinate outlet stream 13.

Immediately upstream with respect to fluid flow in adsorption zone I is the purification zone, defined as the adsorbent between the extract outlet stream 14 and the feed inlet stream 11. The basic operations taking place in the purification zone are the displacement from the non-selective void volume of the adsorbent of any raffinate material carried into this zone and the displacement of any raffinate material retained within the selective pore volume of the molecular sieve. Purification is achieved by passing a portion of extract stream material leaving the desorption zone into the purification zone's upstream boundary to effect the displacement of raffinate material. The flow of liquid in the purification zone is in a downstream direction from the extract outlet stream 14 to the feed inlet stream 11.

Immediately upstream of the purification zone with respect to the fluid flow is the desorption zone. The desorption zone is defined as the adsorbent between the desorbent inlet stream 12 and the extract outlet stream 14. The function of the desorption zone is to allow a desorbent which passes into this zone to displace the extract component retained in the adsorbent during previous contact with feed in the adsorption zone in a prior cycle of operation. The flow of fluid in the desorption zone is essentially in the same direction as that of the prior zones.

The buffer zone is defined as the adsorbent between the raffinate outlet stream 13 and the desorbent inlet stream 12 and is located immediately upstream with respect to the fluid flow to the desorption zone. This zone is utilized to conserve the amount of desorbent utilized in the desorption step since a portion of the raffinate stream which is removed from the adsorption zone can be passed into the buffer zone to displace desorbent present in that zone into the desorption zone. This zone contains enough desorbent to prevent raffinate material present in the raffinate stream 13 from passing out of the adsorption zone into the buffer zone and further from passing into the desorption zone thereby contaminating the extract stream removed from the purification zone.

Figure 2:
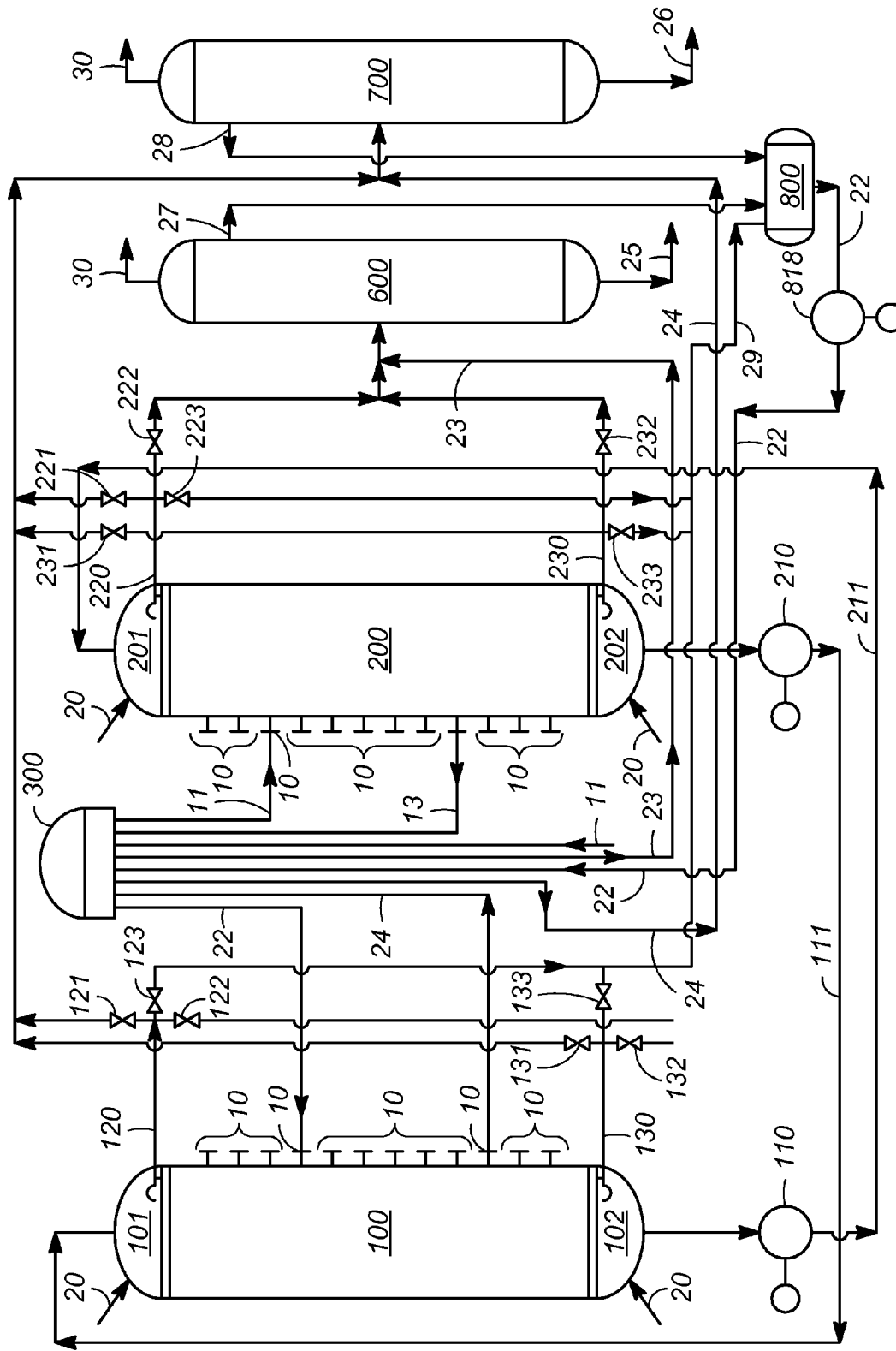
FIG. 2 is a schematic diagram of a simulated moving bed adsorption process using a light desorbent and comprising the features of the invention.

FIG. 2 shows an alternative adsorption-separation process using a light desorbent. The extraction section providing the raffinate and extract streams can be illustrated by essentially the same scheme and description as in FIG. 1, with different numerical designations concomitant with connection to analogous raffinate and extract columns 600 and 700.

A raffinate stream 23 and extract stream 24 on the illustrated scheme contain desorbent in concentrations relative to the respective product from the process of between 0% and 100%. The desorbent generally is separated from raffinate and extract components by fractionation in raffinate column 600 and extract column 700 from the upper portion of each column as illustrated in FIG. 2, preferably as sidestreams 27 and 28 in order to provide dry desorbent to the process; and alternative would be a separate drying column for recycle desorbent. Water and any light materials are removed overhead in streams 30 from each column. A net raffinate product 25 and net extract product 26 have the same compositional characteristics, respectively, as streams 15 and 16 of FIG. 1. Each of the raffinate and extract columns comprise appurtences for condensing and separating the overhead stream and supplying heat to the bottom of the column as known in the art.

Streams 27 and 28 preferably pass to a vessel 800, along with stream 29 discussed subsequently, in order to mitigate any compositional variations. The combined desorbent is returned to the adsorption section from vessel 800 through pump 810 in stream 22.

If the head flush contains valuable components to be recovered according to the present invention, the flow rate is less than 10 volume-%, and generally below 1%, of the circulating fluid; usually the flow rate is around 0.1% or less of the circulating fluid. Thus, the recovery of valuable components according to the invention should have a minor or negligible effect on the operation of the associated process.

The principles of head flushing in the adsorption vessels 100 and 200 are essentially as described in U.S. Pat. No. 7,011,759 B1, incorporated herein by reference thereto. The two vessels comprise in both FIG. 1 and FIG. 2 respectively equalization chambers 101 and 102 in vessel 100 and 201 and 202 in vessel 200, defined by the respective rounded heads and distribution grids of the respective vessels. Head-flush fluid is passed into the respective equalization chambers through conduits 20. A head-flush purge is removed from the respective chambers of vessel 100 via snorkels and conduits 120 and 130 and from vessel 200 via snorkels and conduits 220 and 230.

The purge is distributed sequentially via valving on each of the head-flush purge conduits from each of the chambers to either the extract column, when the purge is consonant with extract-purity standards, or to the raffinate column, when such standards would not be met; when the purge is essentially pure desorbent, it may be sent directly to the desorbent circuit 12. For example, valve 121 is open and valves 122 and 123 are closed with manifolding of purge into conduit 14 when extract recovered from the purge in conduit 120 is consonant with extract-purity standards and valves 121 and 122 would be reversed with manifolding of purge into conduit 13 when such standards are not met. Optionally, valve 123 would be opened and valves 121 and 122 closed when the purge meets desorbent standards. Corresponding open-and-closed determinations would apply for valves 131, 132 and 133, 221, 222 and 223, and 231,232 and 233. Each head-flush purge is distributed to the extract column, raffinate column or desorbent circuit according to the standards described above.

In FIG. 2, the purge meeting desorbent standards is manifolded into conduit 29 which is sent to vessel 800 along with desorbent from columns 600 and 700 as discussed earlier.

The head-flush purge is consonant with extract-purity standards when, after fractionation to separate desorbent in column 500 according to the subject process, the purge would yield extract having specified extract-product purity according to the claims. Conversely, the purge is not consonant with extract-purity standards when the fractionation would not yield such extract product. Each head-flush purge is distributed to the extract column or raffinate column sequentially according to such standards, repeating the steps of the distribution cycle as the composition changes. Optionally, the purge is returned to the desorbent circuit when the concentration of extract in the purge is no more than 3500 weight parts per million and the contained extract has at least the purity of the extract product. Flow of the head-flush fluid may be controlled by analysis of the level of contaminants in the streams via mass spectrometry or other methods known in the art. Control logics represent any of various devices useful to control elements of the system to distribute the purge. For example, control may be by programmable logic controllers (PLCs), computer hardware, computer software, desktop computers, mainframe computers, servers, clients, integrated circuits, or any other appropriate device, either as separate elements or a single device in one location on or outside the system. The control logic may be coupled to other elements to control, for example, the opening and/or closing of valves.

Preferably the distribution of the head-flush fluid is controlled by the rotating disc valve position. The position locates the distribution of feed and desorbent to and removal of the extract and raffinate streams from the adsorbent bed and thus the operational zones. The purge stream is most suitably directed to the extract column when the equalization chamber is adjacent to the purification zone in the adsorbent bed. The distribution of the flush may be set initially with reference to the position of the purification zone, with the timing of the valve sequencing being fine-tuned by analysis of the purge fluid.

The above description and examples are intended to be illustrative of the invention without limiting its scope. The skilled routineer will readily understand how to extrapolate parameters of the disclosure to other embodiments of the invention. The invention is limited only by the claims set forth herein.

The invention claimed is:

1. A process for the adsorption-separation of a feed stream into an extract product, containing a defined ratio of extract to impurities, from a raffinate product, in which a head-flush purge fluid is removed from a process vessel containing an adsorption bed and at least one equalization chamber, comprising:
    I. passing an internal process fluid into the equalization chamber in a process vessel having at least one rounded head,
    II. passing a head-flush fluid into the equalization chamber,
    III. withdrawing a head-flush purge from the equalization chamber comprising varying ratios of the extract and impurities to a withdrawal pump,
    IV. measuring the contained ratio of extract to impurities in the purge, and
    V. distributing the purge through a valving system to:
        (a) a raffinate stream when the weight ratio of extract to impurities in the purge is less than the weight ratio in the extract product, and,
        (b) an extract stream when the weight ratio of extract to impurities in the purge is substantially equal to or greater than the weight ratio in the extract product, and,
    VI. repeating step V according to the determination of the weight ratio of extract to impurities in the purge.

2. The process of claim 1 wherein step V further comprises distributing the purge through a valving system to a desorbent system when the weight ratio of extract to impurities in the purge is substantially equal to or greater than the weight ratio in the extract product and a concentration of extract in the purge is no more than 3500 weight parts per million.

3. The process of claim 1 wherein the extract is para-xylene and the impurities are the sum of the amounts of ethylbenzene, meta-xylene and ortho-xylene.

4. A process for the adsorption-separation of a mixed-C8-aromatics feed stream into a para-xylene product containing a defined ratio of para-xylene to C8-aromatic impurities and a raffinate product, in which a head-flush purge fluid is removed from a process vessel containing an adsorption bed and at least one equalization chamber, comprising:
    I. passing an internal process fluid through into the equalization chamber in a process vessel having at least one rounded head,
    II. passing a head-flush fluid into the equalization chamber,
    III. withdrawing a head-flush purge from the equalization chamber comprising varying ratios of para-xylene and impurities,
    IV. measuring the contained ratio of para-xylene to impurities in the purge, and
    V. distributing the purge through a valving system to:
        (a) a raffinate stream when the weight ratio of para-xylene to impurities in the purge is less than the weight ratio in the extract product, and,
        (b) an extract stream when the weight ratio of para-xylene to impurities in the purge is substantially equal to or greater than the weight ratio in the extract product, and,
    VI. repeating step V according to the determination of the weight ratio of para-xylene to impurities in the purge.

5. The process of claim 4 wherein a purification zone is in a section of the adsorption bed adjacent to the equalization chamber.

6. The process of claim 4 wherein step V further comprises distributing the purge through a valving system to a desorbent system when the weight ratio of extract to impurities in the purge is substantially equal to or greater than the weight ratio in the extract product and the concentration of extract in the purge is no more than 3500 weight parts per million.

7. The process of claim 4 wherein the ratio of para-xylene to impurities in the extract product is at least about 199 to 1.

8. The process of claim 6 wherein the ratio of para-xylene to impurities in the extract product is at least about 999 to 1.

\* \* \* \* \*